United States Patent [19]

Shames et al.

[11] Patent Number: 4,685,448
[45] Date of Patent: Aug. 11, 1987

[54] VOCAL TACTILE FEEDBACK METHOD AND ASSOCIATED APPARATUS

[75] Inventors: George H. Shames; William L. Torgeson, both of Pittsburgh, Pa.

[73] Assignee: University of Pittsburgh, Pittsburgh, Pa.

[21] Appl. No.: 798,240

[22] Filed: Nov. 14, 1985

Related U.S. Application Data

[63] Continuation-in-part of Ser. No. 540,180, Oct. 11, 1983.

[51] Int. Cl.$^4$ ............................................. G09B 19/04
[52] U.S. Cl. ............................ 128/1 R; 128/773; 128/905; 434/185; 181/126
[58] Field of Search ............... 128/715, 773, 905, 1 R; 434/185; 623/9; 181/126; 381/70; 179/107 BC

[56] References Cited

U.S. PATENT DOCUMENTS

| | | | |
|---|---|---|---|
| 2,273,078 | 2/1942 | Wright | 623/9 |
| 2,611,829 | 9/1952 | Hazard | 181/126 |
| 2,678,973 | 5/1954 | Newman | 179/107 BC |
| 3,024,783 | 3/1962 | Timcke | 128/773 |
| 3,030,456 | 4/1962 | Knauert | 179/107 BC |
| 3,453,749 | 7/1969 | Snedeker | 434/185 |
| 4,464,119 | 8/1984 | Vildgrube et al. | 434/185 |

FOREIGN PATENT DOCUMENTS

| | | | |
|---|---|---|---|
| 2260153 | 10/1975 | France | 434/185 |
| 1210171 | 10/1970 | United Kingdom | 623/9 |
| 925338 | 5/1982 | U.S.S.R. | 623/9 |

OTHER PUBLICATIONS

Pollock et al., Biomed. Eng., vol. 11, No. 12, Dec. 1976, pp. 413–414.

*Primary Examiner*—Kyle L. Howell
*Assistant Examiner*—John C. Hanley
*Attorney, Agent, or Firm*—Arnold B. Silverman

[57] ABSTRACT

A vocal tactile feedback apparatus and method for use in the treatment of stuttering and other speech or hearing abnormalities is disclosed. A microphone and amplifier are utilized to produce and amplify an electronic signal responsive to vocal utterances spoken within a known range of the microphone. The amplified signal is then delayed by a suitable delaying circuit for a desired time interval and is then transmitted to an electromechanical transducer attached to the outer surface of the laryngeal or glottis region of the neck of a user. The transducer then transforms the amplified delayed signal into a mechanical vibration to provide delayed vibrotactile feedback of the vocal utterances whether spoken by the user or by others. A unique transducer assembly for use in the apparatus and method is disclosed.

2 Claims, 10 Drawing Figures

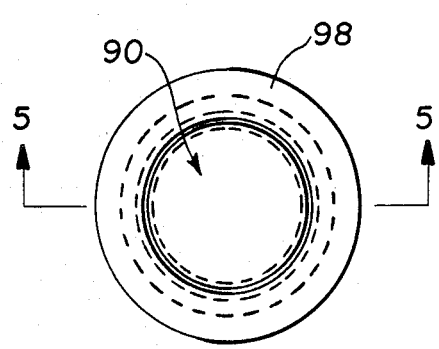
FIG. 4
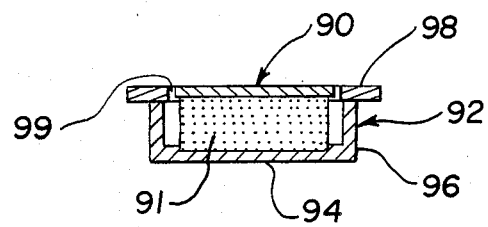
FIG. 5
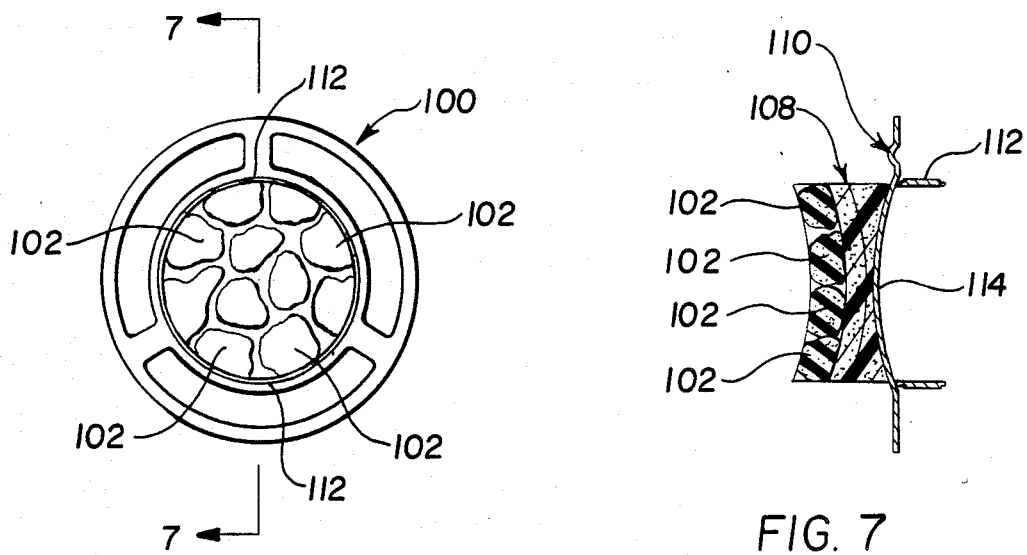
FIG. 6
FIG. 7

VOCAL TACTILE FEEDBACK METHOD AND ASSOCIATED APPARATUS

This application is a continuation-in-part of U.S. Ser. No. 540,180, filed on Oct. 11, 1983, and entitled "Vocal Feedback Method and Associated Apparatus".

BACKGROUND OF THE INVENTION

1. Field of the Invention

This invention relates to a new and improved vocal feedback apparatus and method for use in the treatment of stuttering and other speech and hearing abnormalities.

2. Description of the Prior Art

There are many known devices and methods for aiding persongs having a speech or hearing problem. See generally U.S. Pat. Nos. 3,368,551 and 4,310,002.

It has been known in speech therapy to provide delayed auditory feedback by means of a headphone. See U.S. Pat. No. 4,464,119, Pollock et al., Biomedical Engineering, Vol. 11, No. 12, Dec. 1976, pp. 413–414, and Stuttering: A full cure, PARADE, Sept. 21, 1980, p. 17.

It has been known to provide a switch which permits listening by radio and mastoid bone mediums. French Pat. No. 2,260,133.

U.S. Pat. No. 4,472,833, discloses a system for providing and indication by various means such as a tactile element when the speech rate exceeds a predetermined value.

U.S. Pat. No. 3,267,931 discloses a feedback system which responsive to audio input will provide signals to viable nerves of the facial system.

It has been known in treating certain types of stuttering to measure muscle activity in the lip, chin, larynx and frontalis muscle region and provide an audio signal of a frequency proportional to the level of muscle activity. See Guitar, Journal of Speech and Hearing Research, Vol. 18, No. 4, pp. 672–685, (Dec. 1975).

It has also been known to record surface electromyograms from the larynx, chin, lip and trapezious. The feedback is in the form of a tone generated in response to muscle activity. See Hardyck et al., Feedback of Speech Muscle Activity During Silent Reading: Rapid Extinction, Institute of Human Learning, Univ. of Cal., Berkeley, (Aug. 1967) and Hardyck et al. Science, Vol. 154, pp. 1467–1468, Dec. 16, 1966.

U.S. Pat. No. 4,198,542 discloses a device which can be used either to increase the amplitude of a person's voice by causing a second vocal cord to vibrate at the same frequency as a first cord, or to aid in closng the glottis by increasing the tension of the crico-thyroid muscle and thereby allowing the thyroid cartilege to swing normally. For each use this device uses a pair of transducers and appropriate amplifiers and rectifiers. While this device does utilize transducers, it would not be suitable for use in providing tactile feedback.

Other devices, such as the one disclosed in U.S. Pat. No. 3,626,607, suggest the concept of tactile stimulation. That device amplifies an instructor's vocal utterance and transmits the same through a mechanical transducer to the hands or feet of the recipient by means of a vibrating panel supported on a platform. It does not, however, provide tactile stimulation of or feedback to the glottis.

U.S. Pat. No. 3,453,749 discloses an apparatus and method for use by a speech therapist or instructor in teaching persons having speech abnormalities. That invention involves the electronic amplification of the instructor's vocal utterance and the direct application of amplified vibrations through a throat transducer to the larynx region of the throat. While that device and method are helpful in the treatment of certain types of speech abnormalities, they do not provide a satisfactory solution to the problem of stuttering.

Stuttering is a spasmodic repetition of a vocal utterance as a result of excitement or some impediment. Typically, stuttering is of psychogenic origin and tends to arise particularly during stress during the pre-school years, but it also occurs when a child starts school or with the onset of puberty. Providing tactile stimulation to the laryngeal or glottis region of the throat does not, in and of itself, provide an effective treatment for stuttering. Rather, because of its repetitive nature, to provide an effective treatment for stuttering, tactile feedback of the user's own utterance must be delayed in order to allow the user to utilize the tactile stimulation resulting from his own voice rather than that of a third party.

In spite of these known prior art teachings, there remains a real and substantial need for an effective method and apparatus for the treatment of stuttering and other speech and hearing problems.

SUMMARY OF THE INVENTION

A vocal tactile feedback method for use in the treatment of stuttering and other speech and hearing abnormalities is disclosed. A suitable microphone and amplifier means are provided for producing and amplifying an electronic signal responsive to vocal utterances spoken by either the user or a third party. The signal is delayed for a desired time interval and is then provided to an electro-mechanical transducer attached to the outer surface of the laryngeal region of the neck of the user to provide delayed tactile feedback of the utterance. A unique form of transducer assembly may be employed.

It is an object of the present invention to supply a delayed signal responsive to a vocal utterance to an electro-mechanical transducer which is secured in intimate contact with an outer surface of the laryngeal region of the neck of the user in order to produce delayed tactile feedback of the utterance.

It is another object of the present invention to provide a method and associated apparatus for enhancing the awareness in the user of his or her own and other's vocalizations and phonatory behavior.

It is another object of the invention to provide heightened user awareness by accentuating normal vibratory sensations produced by the larynx by applying delayed and amplified speech signals to the laryngeal region by an external electro-mechanical transducer.

It is yet another object of the invention to provide a method and apparatus for inducing the sensations of normal speech to persons having reduced functionality of the vocal cords or a hearing problem.

It is an object of the present invention to provide a vocal feedback method which can be utilized by the user in the absence of an instructor or any other third party.

It is an other objective of the invention to provide a feedback method wherein the duration of the time interval in which the vocal utterance is delayed may be infinitely varied.

It is yet another object of the present invention to provide apparatus which may be battery energized and includes a microphone, amplifier means, delaying means and a transducer and which may be provided in a compact and readily portable form.

It is a further object of the invention to provide a vocal feedback apparatus having a transducer which can be secured in intimate contact with the user's neck by a suitable elastic strap means or other securing means such as an adhesive or clip, for example.

It is yet another object of the invention to provide an amplifier, battery and digital delay means within a compact housing sized so that it may be easily carried in a pocket of the user.

It is another object of the present invention to provide a vocal tactile feedback device which may be worn by deaf children on a semi-permanent basis in order to capitalize on and enhance the "babble behavior" feedback which all young children receive from their parents.

It is another object of the invention to provide an improved transducer assembly construction which is designed to function efficiently in the present invention.

It is still another object of the invention to provide a vocal tactile feedback device which is economical to produce and efficient in its operation.

These and other objects of the present invention will be more fully understood from the following description of the invention on reference to the illustration appended hereto.

BRIEF DESCRIPTION OF THE DRAWINGS

FIG. 4 is a top plan view of a form of transducer of the present invention.

FIG. 5 is a cross-sectional view of the transducer of FIG. 4 taken through 5—5.

FIG. 6 is a top plan view of a coupler assembly adapted for use with the transducer.

FIG. 7 is a cross-sectional illustration of the coupler assembly of FIG. 6 taken through 7—7.

DESCRIPTION OF THE PREFERRED EMBODIMENTS

Figure 1:
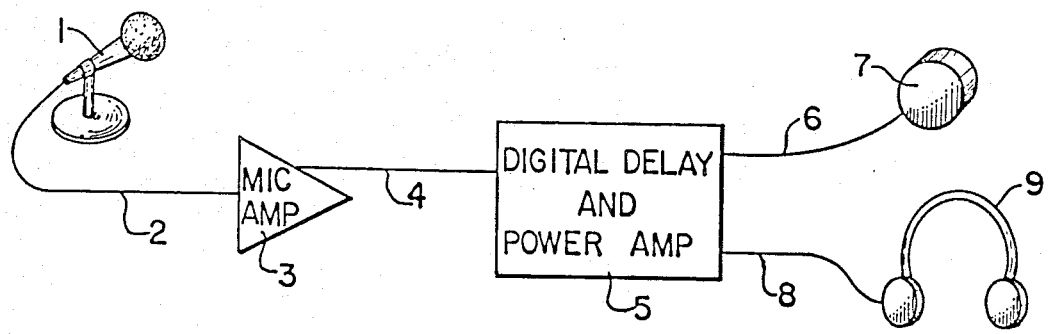
FIG. 1 is a schematic view showing the various components of an apparatus according to the present invention.

Referring specifically to FIG. 1, the apparatus includes a microphone 1 for receiving an audible vocalization and producing an electric signal responsive thereto, a microphone amplifier 3 for amplifying the signal, a digital delay circuit means and a power amplifier, generally referred to as 5, for delaying the signal and amplifying the same to a sufficient power level so that it may effectively drive an electro-mechanical transducer 7. As there are many types of microphone amplifiers which are known in the art and which will function properly in accordance with the present invention no particular type need be illustrated and described herein. Transducer 7 is utilized to produce a mechanical vibration which is responsive to the vocal utterance received by microphone 1.

Line 2 is provided to operably connect microphone 1 to microphone amplifier 3. Line 4 connects microphone amplifier 3 to the digital delay and power amplifier means 5 and line 6 connects the delay and amplifier means 5 to transducer 7.

An optional set of headphones 9 may also be included for providing, through line 8, simultaneous auditory signals corresponding to the mechanical vibrations which are applied to the laryngeal or glottis region of the neck of the user.

Figure 2:
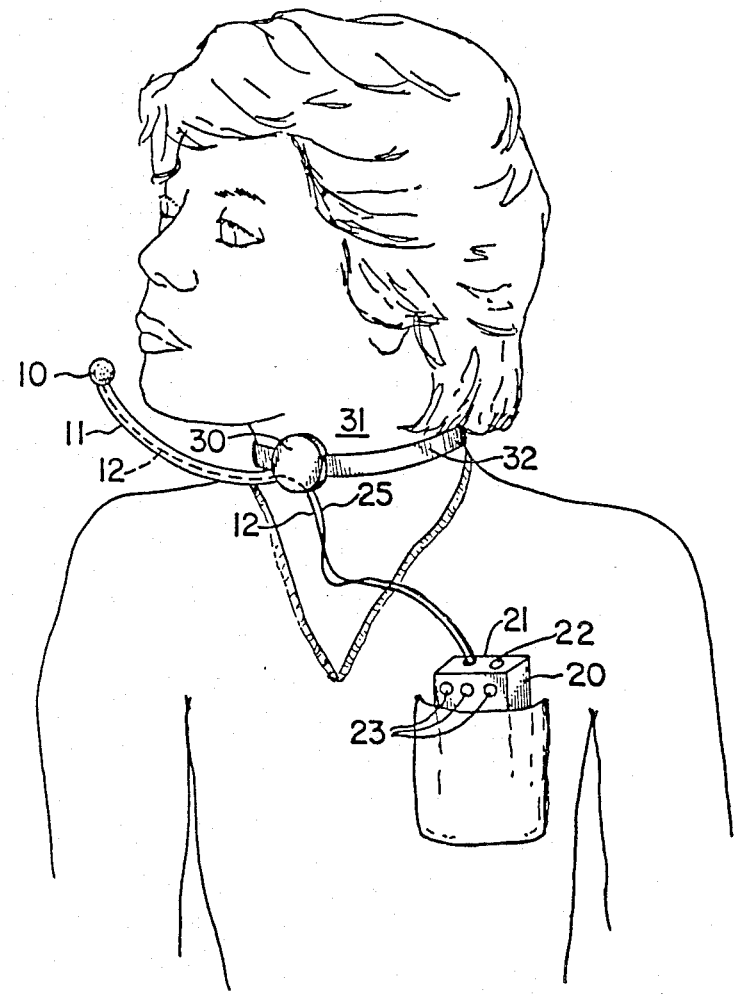
FIG. 2 is a perspective view of one embodiment of the present invention showing a compact and portable delayed tactile vocal feedbck device as worn by a user.

Referring now to FIG. 2, a portable and compact vocal feedback device is shown. The elements of the device are a microphone 10, an electro-mechanical transducer 30 and a housing 20 containing a microphone amplifier, a delay means, a power amplifier and a suitable power supply such as a battery. The transducer 30 in the form shown is provided so as to contact the surface of the user's neck at or near the glottis or laryngeal region 31 thereof. The transducer is secured in intimate contact by an appropriate elastic or adjustable neck strap means 32 or any other suitable securing means, such as a clip or adhesive, for example. Microphone 10 is connected to the transducer 30 by means of microphone support 11 which contains one segment of line 12. The remaining portion of line 12 passes through transducer 30 and is connected to housing 20.

The electrical signal from the microphone is carried by line 12 through the transducer 30 to housing 20 wherein the signal is amplified and delayed. Then the delayed amplified signal is returned through line 25 to the transducer which transforms the amplified signal into responsive mechanical vibration or vibrotactile feedback applied to the user's throat.

Housing 20 may be provided with a number of control means 23 for controlling the amplitude of the amplified signal, the time interval of the delay circuitry and the trebel and bass content of the amplified and delayed signal. An on/off switch (not shown) is also provided. Housing 20 is further provided with an output jack 22 which may be utilized for optional headphones to provide additional audio reinforcement.

Housing 20 is preferably formed to have a generally rectangular cross-sectional configuration and is sized so as to conveniently fit in a shirt pocket of the user as shown. Ideally, the housing of this embodiment should be not greater than about four inches high, not greater than about three inches wide and should be as thin as possible, preferably less than about one-half inch.

Figure 3:
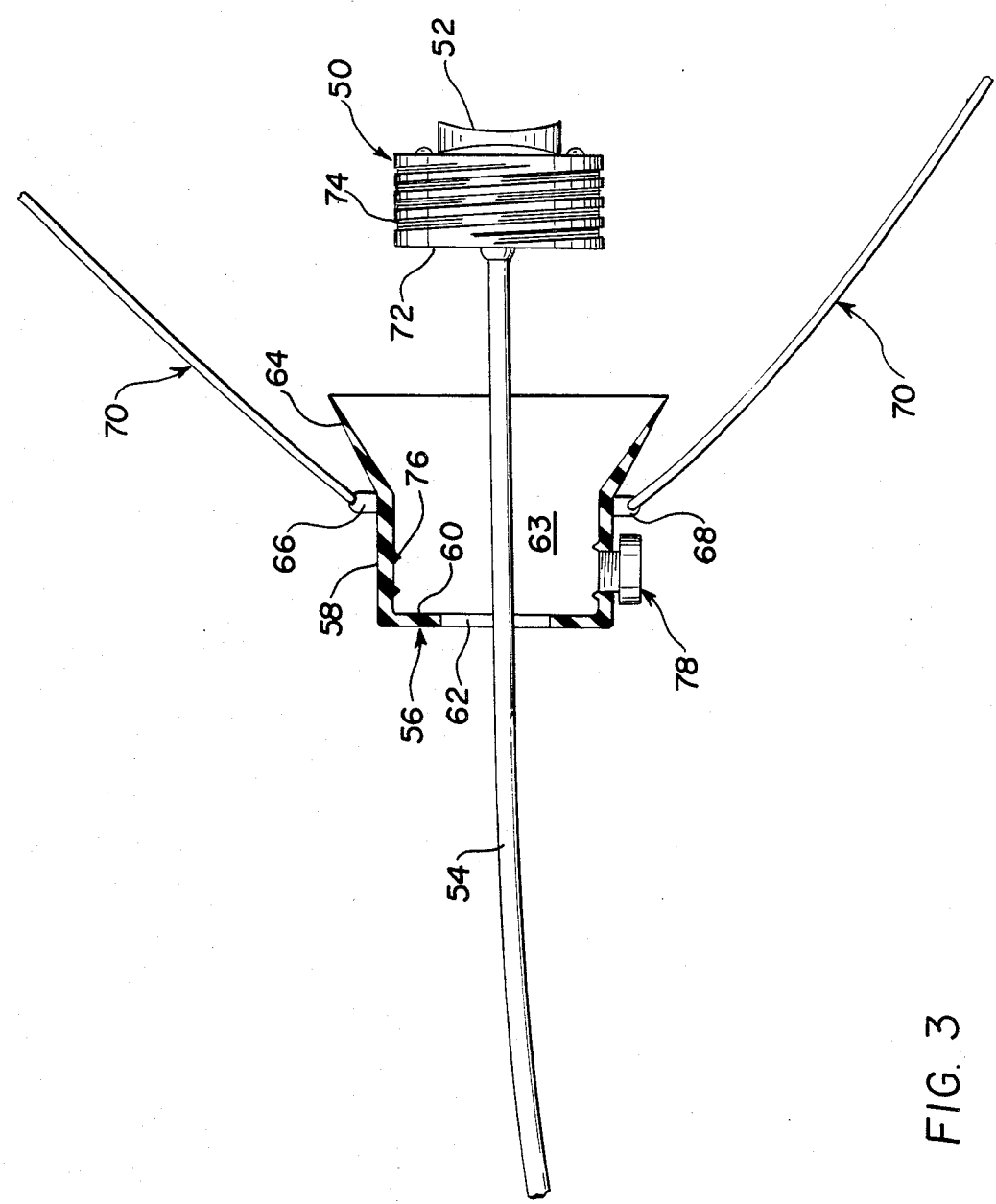
FIG. 3 is an exploded partially schematic view of a transducer assembly of the present invention.

Referring to FIG. 3 in greater detail there is shown a preferred form of transducer assembly. It is desired to provide a relatively shallow transducer assembly, which is electro-mechanically efficient, and relatively light in weight. As is shown in FIG. 3, the transducer assembly 50 is, in the form shown, provided with a coupler 52 which facilitates intimate contact between the transducer assembly and the laryngeal region of the user. The transducer 50 is energized through electrical lead 54 which is connected to a suitable power source.

Referring still to FIG. 3 there is shown a preferred form of transducer retainer assembly. A generally tubular retainer 56 is preferably composed of rubber, such as silicone rubber, metal, such as aluminum, or other suitable material. A threaded metal ferrule may be inserted into a rubber retainer, if desired. When the body 58 and end wall 60 are made of metal, flared portion 64 is preferably made of silicone rubber or a similar elastomeric material which is bonded or otherwise secured to tubular body 58. A tubular body segment 58 cooperates with a flared tubular portion 64 and a transverse end wall 60 which has opening 62 to define a recess 63 which receives the transducer assembly 50. A strap 70 which is adapted to be in intimate engagement with the user's neck is secured to ears 66, 68 of retainer 56. External thread 74 on transducer assembly 50 is threadedly engaged by internal thread 76 on retainer 56. When the desired relative position (generally with wall 72 facing wall 60) is achieved, lock screw 78 is tightened to secure the transducer assembly 50 to the retainer 56. The retainer 56 and transducer assembly 50 should be in such relative position that contact between the vibrating element and the laryngeal region be maintained as the vibrotactile motion occurs, while resisting excessive deflection.

Either by use of an elastic strap 70 or an adjustable length strap 70 or by any other means, the transducer assembly 50 is maintained in intimate contact with the user. Projecting flared portion 64 serves to facilitate maintaining the desired intimate contact between the transducer assembly 50 and the laryngeal region of the user's neck. The flared portion is preferably in resiliently maintained, annularly continuous contact with the user.

Referring to FIGS. 4 and 5, there is illustrated a preferred form of transducer 90 which as a magnetic core 91 and transducer container 92, both of which are disposed within transducer assembly 50 and are separated by coil receiving gap 99. Container 92 has a bottom wall 94, an annular side wall 92 and an annular top wall 98.

The transducer may be of any suitable variety such as piezoelectric, for example. A preferred magnetic material for the transducer is one which is composed of rare earth magnetic materials. Specifically preferred magnetic materials would be those composed of samarium-cobalt or neodymium-iron-boron. It is preferred that the transducer be fabricated with relatively thin magnetic assemblies of high flux densities and that they be relatively light in weight. It is prefered that the transducer assembly employ an open spider type suspension in order to efficiently produce the desired tactile vibrations. The suspension should support the voice coil in proper alignment and minimize the undesired production of sound by vibrating elements. The voice coil is received in gap 99. This may function similar to a voice coil/magnet system such as is used in a high efficiency loudspeaker. The retainer 56 also serves to resist undesired entry of external sound.

It is preferred that the transducer assembly 90 have a coupler such as 52 in FIG. 3 interposed between the transducers 91, 92 and the user in order to enhance intimacy of contact and transmission of the tactile action. Referring to FIGS. 6 and 7 there is shown a preferred form of coupler. A preferred approach is to provide a deformable layer of vibration transmitting material between the transducer and the user's laryngeal region. A suitable material for this purpose is a borosiloxane. Such a material will flow under steady state stresses to establish the desired intimacy of contact between the transducer and the user, while being highly elastic in response to suddenly applied stresses. As a result when the assembly is placed in contact with the user the material will deform to establish intimate surface to surface contact between the material and the user. Tactile excitation will result from transducer vibrations passing through the material with little loss.

In the form shown in FIGS. 6 and 7, the vibration transmitting material is constrained within a plurality of closed cells 102 which face the user.

A substantially rigid coupler 108 which may be composed of polystyrene, for example, is interposed between cells 102 and open spider which has domed center 114 which may preferably be composed of a non-ferrous metal, such as aluminum, and periphery 110. The coupler 108 preferably has exteriorly concave surfaces. Vice coil 112 is mounted on an annular member and is adapted to be disposed in the gap 99 of transducer 90.

It is to be understood that various other forms of the present invention are contemplated. For example a microphone could easily be formed integrally with the transducer thereby eliminating the need for a separate microphone. Additionally, a small transmitter and reciver could be incorporated into the transducer making it fully integrated and operational without the need for any connecting wires.

As mentioned hereinabove, an advantage of providing delay circuitry with a vocal tactile feedback system is to enable the user to provide the vocal utterance thereby eliminating the need to have an instructor or third party involved in the process. This system, therefore, provides a self-instructional device wherein a person responds to input from himself or herself or from a third party. According to the present invention, a method for treating stuttering and other speech or hearing abnormalities includes the steps of providing a suitable microphone and amplifier for producing and amplifying an electronic signal which is responsive to vocal utterances spoken within a known range of the microphone. Delaying the amplified signal with a suitable delaying means for a desired time interval and providing the delayed signal to an electro-mechanical transducer in contact with an outer surface of the glottis or laryngeal region of the neck of a user to provide delayed tactile feedback of the vocal utterance whether spoken by the user or by others is permitted. In the treatment of stuttering, a delay of about 250 milliseconds is preferably employed initially with the amount of the dealy being reduced as treatment progresses. An infinitely variable time delay circuitry is preferred for maximum flexibility.

While it will be readily apparent to those skilled in the art that numerous forms of electrical circuits, delay means and power sources may be employed in the present invention a specific preferred form will be disclosed herein.

Figures 8, 9:
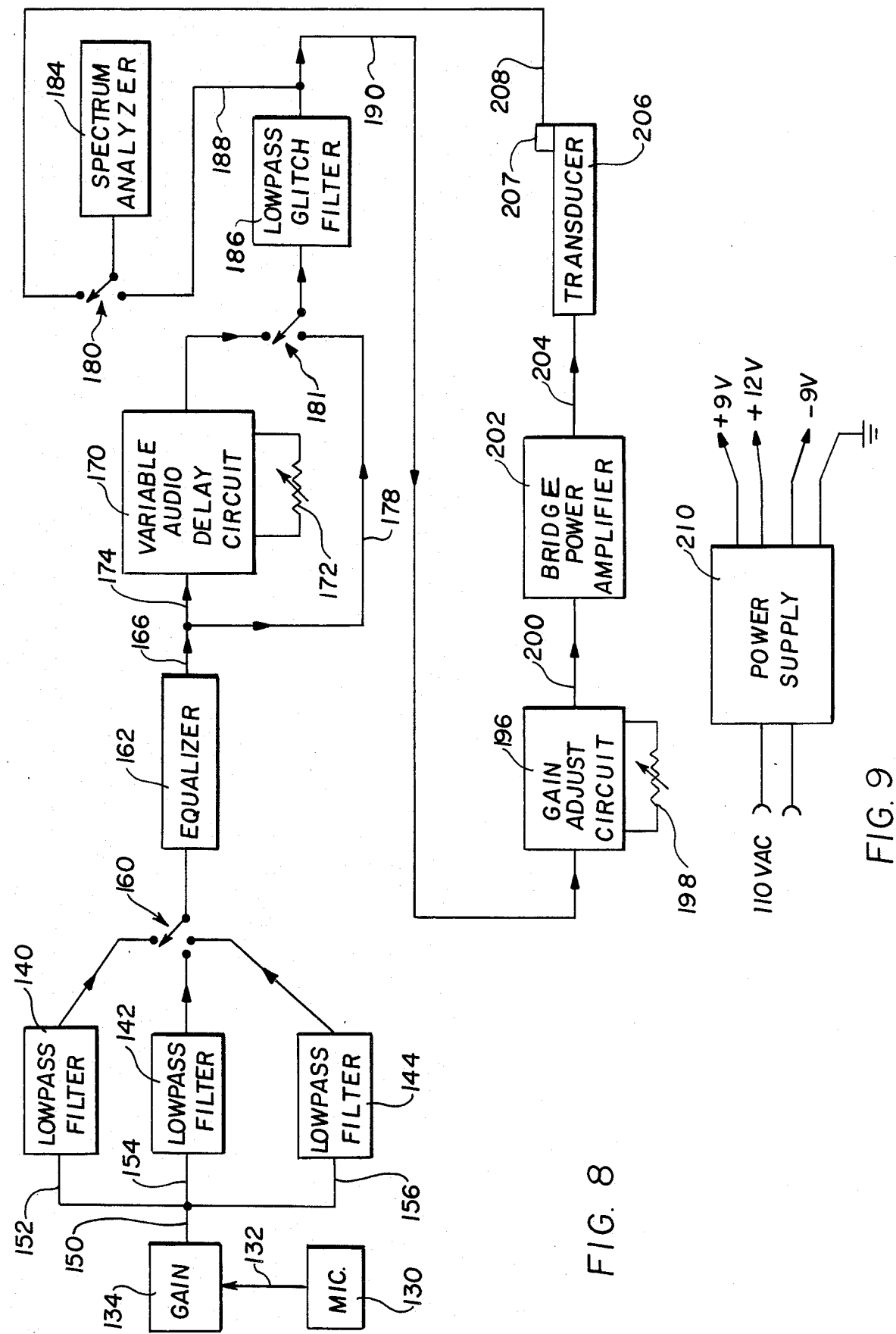
FIG. 8 is a schematic circuit diagram of a form of the present invention.
FIG. 9 is a schematic illustration of a form of power supply.

As is shown in FIG. 8, a signal from microphone 130 which may be a low impedance dynamic type, passes by lead 132 to gain 134 which may be an amplifier having a gain of about 16. Depending upon the position of filter select switch 160 the signal emerging from gain 134 on lead 150 will pass through one of the low pass filters 140, 142, 144. If desired, a single low pass filter could be employed in lieu of filters 140, 142, 144 with switch 160 being eliminated. These filters may, for example, respectively, have cutoff frequencies of 2 KHz, 3 KHz and 4 KHz. These filters limit the high frequencies going to the delay circuit. The signal then passes to equalizer A 162 which may be a 12 band equalizer and by leads 166, 174 to variable audi delay circuit 170 which has delay adjustment 172. The equalizer 162 may be employed to emphasize or de-emphasize selected frequency bands of the user's voice. It also may be employed to reduce acoustic feedback between the microphone and vibration transducer. Depending upon the position of delay select switch 180 the signal on lead 166 entering delay circuit on lead 174 will enter delay circuit 170 and pass through switch 180 to spectrum analyzer 184 or the feedback signal from transducer sensor 207 may be lead 208 enter spectrum analyzer 184. The spectrum analyzer 184 serves to measure spectral content of the electrical signal applied to the transducer. Alternately, the analyzer can display the amplitude spectrum of the tactile vibrations applied to the patient's throat by means of an amplitude sensor such as a strain gauge sensor mounted on the transducer, for example. In this mode of operation, a "pink noise" generator can be advantageously connected at the input system in lieu of the microphone. Reference herein to use of a microphone shall be deemed to embrace such a practice. The analyzer will then yield a direct measure of the amplitude response of the system with uniform energy excitation over the selected frequency band.

The delay circuit may be set to the desired delay period by adjustment means 172. The delay circuit will cause the signal from the microphone to be delayed in reaching the vibration transducer, preferably by up to about 0.5 seconds for example. In treating stuttering, a delay period of about 250 milliseconds, for example, might be employed. Signals passing through the delay circuit 170 when switch 181 is in the "on" position will pass through low pass glitch filter 186 over lead 190 to gain adjust circuit 196 which controls the amount of signal reaching bridge power amplifier 202 on lead and has gain adjustment means 198. The low pass glitch filter 186 may be a 4th order low pass filter with a cutoff frequency of 4 KHz, for example. This filter 186 eliminates any clock frequency component from the dealy circuit 170 that may be mixed with the audio signal. Signals emerging from gain adjust circuit 196 pass over lead 200 to bridge power amplifier 202 which has floating outputs and is used to energize transducer 206. Amplifier 202 output is carried by lead 204 to vibration transducer 206 which coverts the electrical signal to vibrotactile motion vibrations.

The form shown in FIG. 8 is best suited to use in vocal feedback apparatus for clinical application. For compact, battery powered units, such as that shown in FIGS. 1 and 2, there will not normally be provided with an equalizer, a spectrum analyzer or adjustable low pass filters as this minimizes size, weight and power requirements.

FIG. 9 illustrates a suitable power supply 210 for use in the circuit of FIG. 8. The supply has 110 volt AC input and output terminals at +9 volts, −9 volts, +12 volts, −12 volts and ground. This power supply may be employed for all components except the bridge power amplifier 202 which uses +12 volts D.C. Alternately, one or more batteries of suitable voltage may be employed.

Figure 10:
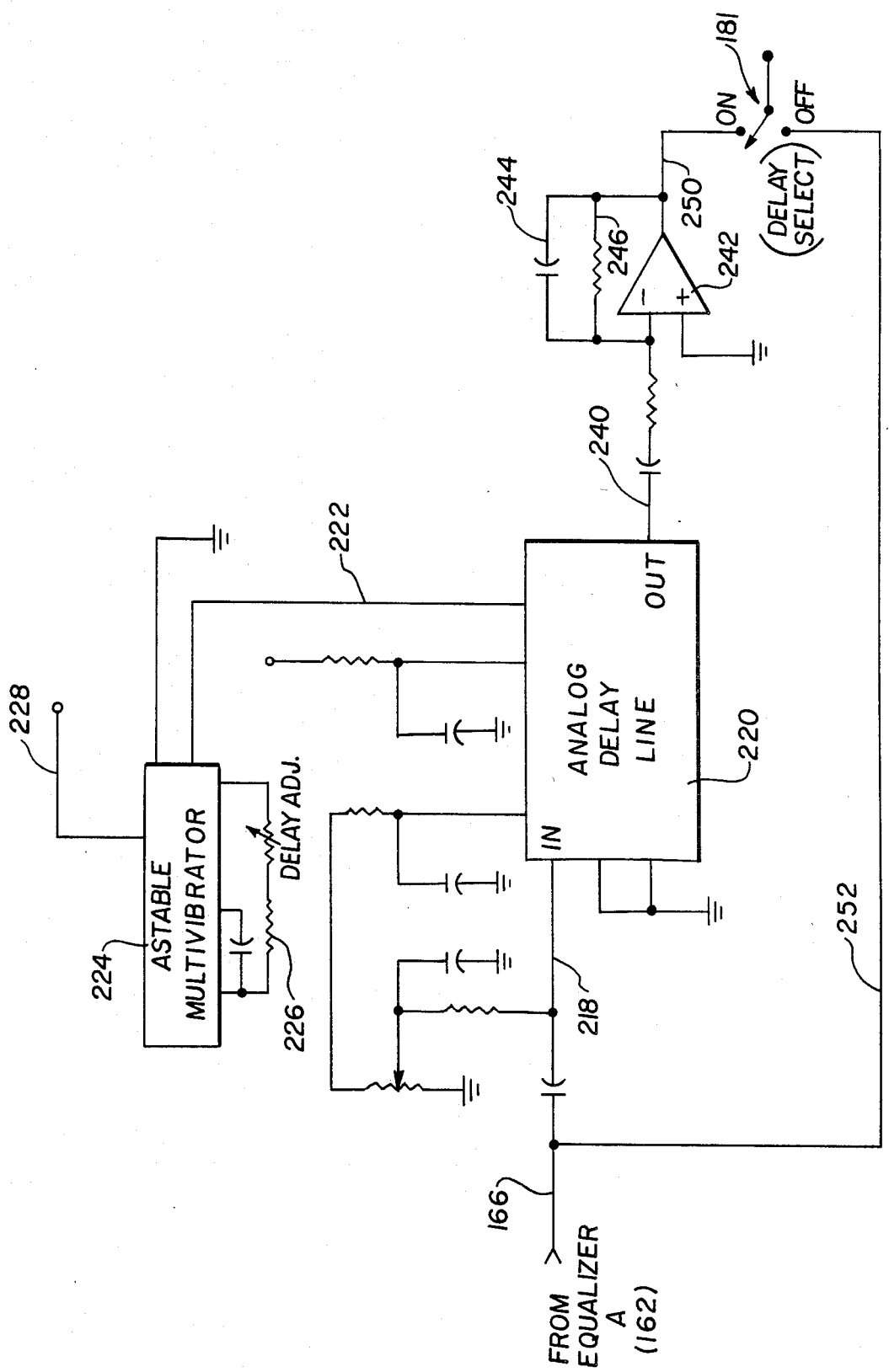
FIG. 10 is a schematic diagram of a form of variable delay circuit.

Referring to FIG. 10, details of a form of delay circuit will be considered employing certain new reference numbers for convenience of reference. The variable time delay circuit shown enables an analog time delay which is preferably adjustable in the range from about 0.03-0.05 sec. A signal from equalizer 152 is introduced into analog delay line 220 by leads 166, 218. The clock frequency is provided by a multivibrator 224 with an adjustable frequency established by adjustment means 226. Lead 228 is at the desired predetermined voltage. Lead 222 connects clock input of analog delay line 220 with multivibrator 224. A standard RD 5108 delay line may be used. If desired, additional stages can be added to improve the accuracy of the delayed output at high frequencies. Thus, the sampling rate can be doubled by adding a second series delay line improving the resolution of the delayed output, particularly at maximum delay. The 'glitch' filter shown in the block diagram serves to smooth the output of the delayed signal. Shorter delays are possible by increasing the clock frequency (zero delay can be obtained by simply bypassing the delay circuit). Lead 240 carries the signal from analog delay line 220 to low pass filter 242 having feedback components 244, 246. Output on lead 250 depending on position of switch 181 may be delivered to equalizer 162 on lead 252.

The bias network connected to lead 218 and delay line 220 shown in the diagram ensures that the input remains positive (the delay line should ideally work between about 5 and 9 v.).

It is contemplated that the present invention may also be useful in the treatment of deaf children. It is envisioned that by providing a portable unit with a compact tactile feedback device on a child's throat, that the "babble behavior" feedback which all young children receive from their parents may be enhanced. As infants grow, many hours are spent by parents in communicating to their children. If tactile stimulation of the glottis or laryngeal region of the child's throat is provided each time the parent communicates verbally with the child, it is believed that the constant external tactile stimulation and the child's self-generated tactile stimulation may prove to be useful in later stages of learning to speak. As the child grows older the device may then be utilized witht he delay circuitry so that the child, without the aid of a therapist or teacher, may practice various vocalization skills and then receive subsequent tactile feedback of such vocalizations.

It will be appreciated that the present device and associated method permit the use of a relatively small, unobtrusive device. The use of throat and/or lavalier microphones is facilitated. This provides psychological benefits in desensitizing anxiety in stress-inducing situations requiring speech. This is of particular importance with respect to stutterers. It also facilitates use for prolonged periods of time in a wide variety of environments.

It will be appreciated that the present invention by employing tactile feedback, as distinguished from solely auditory feedback is based upon different neurological systems and phenomena in different parts of the body.

While for clarity of disclosure a particular form of microphone has been illustrated, it will be appreciated that numerous types of microphones may be employed in the present invention. A throat microphone, for example, may be employed advantageously, if desired.

Whereas particular embodiments of the invention have been described above for purposes of illustration, it will be appreciated by those skilled in the art that numerous variations of the details may be made without departing from the invention as described in the appended claims.

We claim:

1. A vocal tactile feedback method for use in the treatment of speech or hearing abnormalities or otherwise enhancing speech operability of a person through providing enhanced awareness of phonatory behavior to the person comprising the steps of providing a microphone for producing an electronic signal responsive to the person's vocal utterances, providing amplifier means for amplifying said electronic signal, delaying said amplified signal with delaying circuit means for a desired time interval, progressively during the overall course of said treatment reducing the duration of said time interval, and providing said delayed signal to an electro-mechanical transducer disposed in contact with an outer surface of the laryngeal region on the neck of the person to provide delayed tactile feedback to the person of the said vocal utterances which may be spoken by the person, whereby the feedback will enhance the awareness of the person of said vocal utterances.

2. A vocal tactile feedback method according to claim 1 including employing an initial said time interval of about 250 milliseconds.

* * * * *

UNITED STATES PATENT AND TRADEMARK OFFICE
CERTIFICATE OF CORRECTION

PATENT NO. : 4,685,448

DATED : August 11, 1987

INVENTOR(S) : GEORGE H. SHAMES and WILLIAM L. TORGESON

It is certified that error appears in the above-identified patent and that said Letters Patent is hereby corrected as shown below:

On the Title Page, change the Assignee from "University of Pittsburgh" to --Foundation for Applied Science and Technology--.

Column 1, line 17, "persongs" should be --persons--.

Column 1, line 28, "and" should be --an--.

Column 1, line 41, "trapezious" should be --trapezius--.

Column 1, line 51, "closng" should be --closing--.

Column 3, line 36, "feedbck" should be --feedback--.

Column 4, line 39 "trebel" should be --treble--.

Column 5, line 28, "as" should be --has--.

UNITED STATES PATENT AND TRADEMARK OFFICE
CERTIFICATE OF CORRECTION

PATENT NO. : 4,685,448

DATED : August 11, 1987

INVENTOR(S) : GEORGE H. SHAMES and WILLIAM L. TORGESON

It is certified that error appears in the above-identified patent and that said Letters Patent is hereby corrected as shown below:

Column 5, line 41, "prefered" should be --preferred--.

Column 6, line 13, a comma --,-- should be inserted after "For example".

Column 6, line 17, "reciver" should be --receiver--.

Column 6, line 42, "dealy" should be --delay--.

Column 6, line 63, "audi" should be --audio--.

Column 7, line 33, "dealy" should be --delay--.

Column 7, line 39, "coverts" should be --converts--.

Column 8, line 5, "'glitch'" should be --"glitch"--.

Column 8, line 32, "witht he" should be --with the--.

Signed and Sealed this

Twelfth Day of July, 1988

Attest:

DONALD J. QUIGG

*Attesting Officer*     *Commissioner of Patents and Trademarks*